United States Patent
Gallagher et al.

(10) Patent No.: US 6,706,258 B1
(45) Date of Patent: Mar. 16, 2004

(54) SHAMPOO COMPOSITIONS COMPRISING AND EMULSIFIED SILICONE AN A MICROEMULSIFIED SILICONE

(75) Inventors: Peter Gallagher, Buxtehude (DE); Tipawan Kreu-Nopakun, Bangkok (TH); Andrew Malcolm Murray, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 517 days.

(21) Appl. No.: 09/294,173

(22) Filed: Apr. 19, 1999

(30) Foreign Application Priority Data

Apr. 20, 1998 (GB) .............................................. 9808310

(51) Int. Cl.$^7$ ................................................ A61K 7/06
(52) U.S. Cl. ................ 424/70.1; 424/70.11; 424/70.12; 424/70.21; 424/70.22; 424/70.4; 424/401; 424/404; 514/63; 514/852; 514/880; 514/881; 510/122; 510/123
(58) Field of Search ............................... 424/70.1, 70.4, 424/70.11, 70.12, 70.21, 70.22, 401, 404; 514/852, 63, 880, 881; 510/122, 123

(56) References Cited

U.S. PATENT DOCUMENTS

| | | |
|---|---|---|
| 3,958,581 A | 5/1976 | Abegg et al. |
| 3,962,418 A | 6/1976 | Birkofer |
| 4,009,256 A | 2/1977 | Nowak, Jr. et al. |
| 5,085,857 A | 2/1992 | Reid et al. |
| 5,246,694 A * | 9/1993 | Birtwistle et al. |
| 5,756,436 A * | 5/1998 | Royce et al. |
| 5,776,443 A * | 7/1998 | Vinski et al. |
| 5,977,038 A * | 11/1999 | Birtwistle et al. |
| 5,980,877 A * | 11/1999 | Baravetto et al. |
| 6,004,544 A * | 12/1999 | Schrader et al. |

FOREIGN PATENT DOCUMENTS

| | | |
|---|---|---|
| EP | 0432951 | 6/1991 |
| EP | 0460683 | 12/1991 |
| EP | 0674898 | 10/1995 |
| EP | 0498119 | 3/1996 |
| EP | 0529883 | 1/1997 |
| EP | 0567326 | 1/1998 |
| JP | 05/310533 | 11/1993 |
| WO | 92/10162 | 6/1992 |
| WO | 95/22311 | 8/1995 |
| WO | 95/23581 | 9/1995 |
| WO | 98/18443 | 5/1998 |

OTHER PUBLICATIONS

International Search Report Application No. PCT/EP 99/02281 mailed Jul. 29, 1999.

* cited by examiner

Primary Examiner—Thurman K. Page
Assistant Examiner—Lakshmi Channavajjala
(74) Attorney, Agent, or Firm—Milton L. Honig

(57) ABSTRACT

An aqueous shampoo composition comprising, in addition to water:

i) at least one cleansing surfactant;
  ii) a cationic deposition polymer, and
  iii) a silicone component consisting of a blend of:
   (a) emulsified particles of an insoluble silicone, in which the emulsified particles of insoluble silicone are incorporated into the shampoo composition as a preformed aqueous emulsion having an average silicone particle size in the emulsion and in the shampoo composition of from 0.15 to 30 microns, and
   (b) microemulsified particles of an insoluble silicone, in which the microemulsified particles of insoluble silicone are incorporated into the shampoo composition as a preformed aqueous microemulsion having an average-silicone particle size in the microemulsion and in the shampoo composition of less than 0.10 microns.

17 Claims, No Drawings

6,706,258 B1

SHAMPOO COMPOSITIONS COMPRISING AND EMULSIFIED SILICONE AN A MICROEMULSIFIED SILICONE

FIELD OF THE INVENTION

This invention relates to shampoo compositions, and more particularly to shampoo compositions containing emulsified particles of silicone, which compositions condition the hair leaving it softer and more manageable.

BACKGROUND AND PRIOR ART

The use of silicones as conditioning agents in cosmetic formulations is well known and widely documented in the patent literature. Generally, dispersed droplets of the silicone oil are suspended in the composition, which is then applied to the hair to deposit the silicone material on the hair shaft.

A typical method of silicone shampoo manufacture is disclosed in WO 92/10162. Essentially, the silicone material is emulsified directly into the shampoo by an in situ hot process, in which the complete shampoo mixture incorporating the silicone is mixed thoroughly at elevated temperature, pumped through a high shear mill and then cooled. The silicone can be dispersed in a first process stage with anionic surfactant and fatty alcohol to form a premix. The premix is then mixed with the remaining materials of the shampoo, pumped through a high shear mill, and cooled to obtain the final composition.

A disadvantage associated with an in situ hot process such as is described in WO 92/10162 is that factory handling of viscous silicone oil is difficult in the context of a full shampoo manufacturing operation.

A further disadvantage is that special equipment is normally needed to control silicone particle size during manufacture. GB 2 170 216 A discloses a similar process, in which the full shampoo composition incorporating insoluble, non-volatile silicone is sheared with a high shear mixer until the silicone particles are on average less than 2 microns in diameter. The particle size distribution is then said to be from about 2 to about 55 microns.

In order to solve the above mentioned problems with in situ hot processing of silicone, the alternative of incorporating the silicone as a preformed aqueous emulsion has been proposed. Such a method has the consequences that the silicone is incorporated with a predeterminable, controllable particle size distribution. The silicone is insoluble and remains emulsified in the fully formulated shampoo composition, and thus the step of high shear processing of the silicone within the fully formulated shampoo composition is not required. This also makes manufacture of the compositions easier.

A typical method for incorporating insoluble, non-volatile silicone materials into a conditioning shampoo is disclosed in U.S. Pat. No. 5,085,087 in which such materials are incorporated in the shampoo composition as a pre-formed aqueous emulsion of average particle size less than 2 microns. All the ingredients are mixed in a simple hot or cold process in which the average particle size of the silicone material in the emulsion remains the same in the final shampoo composition.

EP 0 529 883 A1 discloses hair shampoo compositions made by an equivalent method and comprising microemulsified particles of silicone having a particle size of 0.15 microns or less, e.g., 0.036 microns. Reducing the silicone particle size still further in this way is said to improve stability, optical properties and conditioning performance. In particular, the small particle size of these silicone microemulsions means that a suspending system (such as waxy materials, inorganic particles and/or polymeric thickeners) is not required. Also, these silicone microemulsions do not scatter light and can be used for formulating transparent products. The silicone emulsions disclosed in U.S. Pat. No. 5,085,087 are not microemulsions and require a suspending system in the shampoo.

A problem encountered with the above formulations is that the conditioning performance may be insufficient for many people, particularly in regions such as Japan and South East Asia where consumers desire a high level-of conditioning and a "weighty" feel to their hair.

We have now found that the conditioning performance of silicone in a surfactant-based shampoo composition can be significantly boosted by utilising a combination of emulsified silicone and microemulsified silicone, in the shampoo composition.

Advantageously, we have also found that this offers a route to enhanced deposition of other benefit agents such as solid active agents.

SUMMARY OF THE INVENTION

The invention provides an aqueous shampoo composition comprising, in addition to water:
 i) at least one cleansing surfactant;
 ii) a cationic deposition polymer, and
 iii) a silicone component consisting of a blend of:
  (a) emulsified particles of an insoluble silicone, in which the emulsified particles of insoluble silicone are incorporated into the shampoo composition as a preformed aqueous emulsion having an average silicone particle size in the emulsion and in the shampoo composition of from 0.15 to 30 microns, and
  (b) microemulsified particles of an insoluble silicone, in which the microemulsified particles of insoluble silicone are incorporated into the shampoo composition as a preformed aqueous microemulsion having an average silicone particle size in the microemulsion and in the shampoo composition of less than 0.10 microns.

DETAILED DESCRIPTION OF THE INVENTION

Silicone Component

The silicone component consists of a blend of emulsified particles of insoluble silicone of specified average silicone particle size and microemulsified particles of insoluble silicone of specified average silicone particle size.

The silicones are insoluble in the aqueous matrix of the shampoo composition and so are present in emulsified and microemulsified forms respectively, with the silicones present as dispersed particles.

Particle size may be measured by means of a laser light scattering technique, using a 2600D Particle Sizer from Malvern Instruments. The measure of average particle size using this technique is the "D50" value.

Suitable silicones for the silicone component include polydiorganosiloxanes, in particular polydimethylsiloxanes which have the CTFA designation dimethicone. Aminofunctional silicones which have the CTFA designation amodimethicone, are also suitable for use in the compositions of the invention, as are polydimethyl siloxanes having hydroxyl end groups, which have the CTFA designation dimethiconol. Also suitable for use are silicone gums having a slight degree of cross-linking, as are described for example in WO 96/31188. These materials can impart body, volume and stylability to hair, as well as good wet and dry conditioning.

The emulsified particles of insoluble silicone may be of the same silicone type as the microemulsified particles of insoluble silicone, or may be different.

Suitable silicone emulsions and microemulsions for use in the invention are commercially available in a pre-emulsified form. Such pre-formed emulsions can then be incorporated into the shampoo composition by simple mixing, which is particularly advantageous for ease of processing. Pre-formed emulsions are available from suppliers of silicone oils such as Dow Corning, General Electric, Union Carbide, Wacker Chemie, Shin Etsu, Toshiba, Toyo Beauty Co, and Toray Silicone Co.

An aqueous emulsion is the preferred form for such a pre-formed emulsion. In such emulsions, it is usual that the emulsion additionally includes at least one emulsifier in order to stabilise the silicone emulsion.

Suitable emulsifiers are well known in the art and include anionic and nonionic surfactants. Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers for the silicone particles are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

The viscosity of the silicone itself (not the emulsion/microemulsion or the final shampoo composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Viscosity can be measured by means of a glass capillary viscometer as set out further in Dow Corning Corporate Test Method CTM004 Jul. 20, 1970.

The average silicone particle size of the emulsified silicone in the shampoo composition is suitably less than 20 microns, preferably less than 10 microns. Ideally it ranges from 0.15 to 2 microns, optimally from 0.2 to 1 micron.

Examples of suitable pre-formed emulsions include emulsions DC2-1766, DC2-1784, and DC2-1310, all available from Dow Corning. These are all emulsions of dimethiconol. DC2-1766 and DC2-1784 each have an average silicone particle size in the emulsion of less than 2 microns. DC2-1310 has an average silicone particle size in the emulsion of about 8 microns. Cross-linked silicone gums are also available in a pre-emulsified form. A preferred example is the material available from Dow Corning as DC X2-1787, which is an emulsion of cross-linked dimethiconol gum having an average silicone particle size in the emulsion of about 0.5 microns.

The average silicone particle size of the microemulsified silicone in the shampoo composition is suitably less than 0.075 micron. Ideally it ranges from 0.01 to 0.075 micron, optimally from 0.02 to 0.05 micron.

Examples of suitable pre-formed microemulsions include microemulsions DC2-1865 and DC2-1870, available from Dow Corning. These are microemulsions of dimethiconol. DC2-1865 and DC2-1870 each have an average silicone particle size in the microemulsion of less than 0.075 microns. Cross-linked silicone gums are also available in a pre-microemulsified form, which is advantageous for ease of formulation. A preferred example is the material available from Dow Corning as DC X2-1391, which is a microemulsion of cross-linked dimethiconol gum having an average silicone particle size in the microemulsion of about 0.045 microns.

Silicone Ratios

We have found that the conditioning performance of silicone in a surfactant-based shampoo composition can be significantly boosted by utilising a combination of emulsified silicone and microemulsified silicone, in the shampoo composition.

The weight ratio of emulsified particles of silicone to microemulsified particles of silicone suitably ranges from 4:1 to 1:4. Preferably, the ratio of emulsified particles of silicone to microemulsified particles of silicone ranges from 3:1 to 1:3, more preferably from 2:1 to 1:1.

Silicone Levels

The shampoo compositions of the invention typically contain from 0.05 to 5%, preferably from 0.1 to 3%, more preferably from 0.25 to 2%, by weight emulsified particles of silicone based on the total weight of the shampoo composition.

The level of microemulsified particles of silicone in shampoo compositions of the invention is typically from 0.05 to 5%, preferably from 0.1 to 3%, more preferably from 0.25 to 2%, by weight microemulsified particles of silicone based on the total weight of the shampoo composition.

The total amount of silicone (emulsified particles and microemulsified particles) incorporated into the shampoo compositions of the invention depends on the level of conditioning desired and the material used. A preferred amount is from 0.01 to about 10% by weight based on the total weight of the shampoo composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight based on the total weight of the shampoo composition is a suitable level.

Cleansing Surfactant

Shampoo compositions of the invention comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount up to about 5% by weight based on the total weight of the shampoo composition.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO—(G)$_n$ wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose. The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifier for the silicone component) in shampoo compositions of the invention is generally from 0.1 to 50% by weight, preferably from 5 to 30%, more preferably from 10% to 25% by weight based on the total weight of the shampoo composition.

Cationic Deposition Polymer

A cationic deposition polymer is an essential ingredient in shampoo compositions of the invention. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:
  copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide- and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides(as described in WO95/22311). Other cationic deposition polymers that can be used include cationic polysaccharide polymers, such as cationic cellulose derivatives, cationic starch derivatives, and cationic guar gum gerivatives.

Cationic polysaccharide polymers suitable for use in compositions of the-invention include those of the formula:

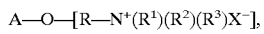

A—O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhodia (formerly Rhone-Poulenc) in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

The cationic deposition polymer will generally be present at levels of from 0.001 to 5%, preferably from about 0.01 to 1%, more preferably from about 0.02% to about 0.5% by weight based on the total weight of the shampoo composition.

Optional Ingredients
Further (Non-silicone) Conditioning Agents

As used herein, the term "conditioning agent" includes any material which is used to give a particular conditioning benefit to hair and/or skin. For example, in compositions for use in washing hair, such as shampoos and conditioners, suitable materials are those which deliver one or more benefits relating to shine, softness, combability, wet-handling, anti-static properties, protection against damage, body, volume, stylability and manageability.

A preferred class of conditioning agents are per-alk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into the compositions of the invention depends on the level of body and volume enhancement desired and the specific material used. A preferred amount is from 0.01 to about 10% by weight based on the total weight of the shampoo composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight based on the total weight of the shampoo composition is a particularly suitable level.

Solid Active Agents

These are a particularly preferred class of optional ingredient in shampoo compositions of the invention.

Surprisingly we have found that the shampoo compositions of the invention can offer a route to enhanced deposition and delivery of such solid active agents as the heavy metal salts of pyridinethione, especially zinc pyridinethione. These are a particularly preferred class of solid antimicrobial and widely used in antidandruff shampoos.

The improved deposition and delivery of solid active agents such as zinc pyridinethione observed with shampoo compositions of the invention means that the level of solid active agent in the shampoo composition can be reduced if desired. This offers particular advantages such as reduced formulational cost and improved shampoo aesthetic appearance.

Other suitable solid active agents include other solid antimicrobials such as climbazole, piroctone olamine, selenium sulphide and ketoconazole. These substances typically have an average particle diameter of from about 0.2 to about 50 microns, preferably from about 0.4 to about 10 microns.

Antimicrobial agents such as zinc pyridinethione are geenerally employed in shampoo compositions in an amount of up to about 2%, e.g. from 1 to 2%, by weight based on the total weight of the shampoo composition.

Advantageously, the enhanced deposition and delivery of solid active agents such as zinc pyridinethione which we have observed from shampoo compositions of the invention means that the level of antimicrobial agent can be reduced if desired, e.g. to a level of from 0.05 to 0.8%, preferably from 0.1 to 0.5%, optimally about 0.3% by weight based on the total weight of the shampoo composition.

Other suitable solid active agents include pigment particles, such as solid dyes or colorants suitable for application to hair, and metal colloids.

Aesthetic Agents

Hair treatment compositions such as shampoos and are frequently opacified or pearlised to enhance consumer appeal.

Examples of opacifying agents include higher fatty alcohols (e.g. cetyl, stearyl, arachidyl and behenyl), solid esters (e.g. cetyl palmitate, glyceryl laurate, stearamide MEA-stearate), high molecular weight fatty amides and alkanolamides and various fatty acid derivatives such as propylene glycol and polyethylene glycol esters. Inorganic materials used to opacify hair treatment compositions include magnesium aluminium silicate, zinc oxide, and titanium dioxide.

Pearlescing agents typically form thin, platelet-type crystals in the composition, which act like tiny mirrors. This gives the pearl lustre effect. Some of the opacifying agents listed above may also crystallise as pearlescing agents, depending on the media in which they are used and the conditions employed.

Typical pearlescing agents may be selected from C16–C22 fatty acids (e.g. stearic acid, myristic acid, oleic acid and behenic acid), esters of C16–C22 fatty acid with alcohols and esters of C16–C22 fatty acid incorporating such elements as alkylene glycol units. Suitable alkylene glycol units may include ethylene glycol and propylene glycol. However, higher alkylene chain length glycols may be employed. Suitable higher alkylene chain length glycols include polyethylene glycol and polypropylene glycol.

Examples are polyethylene glycol mono or diesters of C16–C22 fatty acids having from 1 to 7 ethylene oxide units, and ethylene glycol esters of C16–C22 fatty acids. Preferred esters include polyethylene glycol distearates and ethylene glycol distearates. Examples of a polyethylene glycol distearate available commercially are EUPERLAN PK900 (ex Henkel) or GENAPOL TS (ex Hoechst). An example of an ethylene glycol distearate is EUPERLAN PK3000 (ex Henkel).

Other pearlescing agents include alkanolamides of fatty acids having from 16 to 22 carbon atoms, (e.g. stearic monoethanolamide, stearic diethanolamide, stearic monoisopropanolamide and stearic monoethanolamide stearate); long chain esters of long chain fatty acids (e.g. stearyl stearate, cetyl palmitate); glyceryl esters (e.g. glyceryl distearate), long chain esters of long chain alkanolamides (e.g. stearamide DEA distearate, stearamide MEA stearate), and alkyl (C18–C22) dimethyl amine oxides (e.g. stearyl dimethyl amine oxide).

Further suitable pearlescing agents include inorganic materials such as nacreous pigments based on the natural mineral mica. An example is titanium dioxide coated mica. Particles of this material may vary in size from 2 to 150 microns-in diameter. In general, smaller particles give rise to a pearly appearance, whereas particles having a larger average diameter will result in a glittery composition.

Suitable titanium dioxide coated mica particles are those sold under the trade names TIMIRON (ex Merck) or FLAMENCO (ex Mearl).

The level of opacifying or pearlising agent employed in compositions of the invention is generally from 0.01 to 20%, preferably 0.01 to 0.5%, by weight based on the total weight of the shampoo composition.

Other Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, and sunscreens. Each of these ingredients will be present in an amount effective to accomplish its purpose. Generally these optional ingredients are included individually at a level of up to about 5% by weight based on the total weight of the shampoo composition.

The present invention will now be further illustrated by reference to the following non-limiting Examples. All amounts given are in % by weight based on the total weight of the shampoo composition, unless otherwise stated.

EXAMPLES

Example 1

A shampoo composition was prepared by mixing the following components in the amounts stated.

| Component | % by weight |
| --- | --- |
| Sodium lauryl ether sulphate 2EO | 8.0 |
| Cocamidopropyl betaine | 4.0 |
| Jaguar C13S[1] | 0.3 |
| Silicone emulsion[2] | 2.5 |
| Silicone microemulsion[3] | 6.0 |
| Preservative, pH adjuster, colour, fragrance | q.s. |
| Water | to 100% |

Example 2

A shampoo composition was prepared by mixing the following components in the amounts stated.

| Component | % by weight |
| --- | --- |
| Sodium lauryl ether sulphate 2EO | 12.0 |
| Cocamidopropyl betaine | 1.0 |
| Jaguar C13S[1] | 0.1 |
| CARBOPOL 980[4] | 0.5 |
| Silicone emulsion[5] | 0.83 |
| Silicone microemulsion[3] | 1.6 |
| Zinc pyrithione[6] | 0.625 |
| Sodium chloride | 2.0 |
| DL-Panthenol | 0.1 |
| Vitamin E acetate | 0.05 |
| Preservative, pH adjuster, colour, fragrance | q.s. |
| Water | to 100% |

[1] Jaguar C13S is guar hydroxypropyltrimonium chloride available from Rhodia (formerly Rhone-Poulenc)

[2] Introduced as BY22-048 from Toray Silicone Co., an emulsion (60% a.i.) of dimethicone (silicone viscosity 1 million cst, average silicone particle size 0.5 micron).

[3] Introduced as DC2-1870 from Dow Corning Ltd., a microemulsion (25% a.i.) of dimethiconol (silicone viscosity 60,000 million cst, average silicone particle size 0.04 micron) in anionic/nonionic surfactant (TEA-dodecylbenzene sulphonate/Laureth-23).

(4) CARBOPOL 980 is a cross-linked polyacrylate available from B F Goodrich.

(5) Introduced as DC2-1766 from Dow Corning Ltd., an emulsion (60% a.i.) of dimethiconol (silicone viscosity 1 million cst, average silicone particle size 0.5 micron) in anionic surfactant (sodium lauryl sulphate).

(6) Supplied as Zinc Omadine, Fine Particle Size Grade, (48% a.i.) from Olin Corporation.

What is claimed is:

1. An aqueous shampoo composition comprising, in addition to water:
   i) at least one cleansing surfactant;
   ii) a cationic deposition polymer, and
   iii) a silicone component consisting of a blend of:
      (a) emulsified particles of an insoluble silicone, in which the emulsified particles of insoluble silicone are incorporated into the shampoo composition as a preformed aqueous emulsion having an average silicone particle size in the emulsion and in the shampoo composition of from 0.15 to 30 microns, and
      (b) microemulsified particles of an insoluble silicone, in which the microemulsified particles of insoluble silicone are incorporated into the shampoo composition as a preformed aqueous microemulsion having an average silicone particle size in the microemulsion and in the shampoo composition of less than 0.10 microns.

2. A composition according to claim 1, in which the average silicone particle size of the emulsified silicone in the shampoo composition ranges from 0.15 to 2 microns.

3. A composition according to claim 1, in which the average silicone particle size of the microemulsified silicone in the shampoo composition ranges from 0.01 to 0.075 micron.

4. A composition according to claim 1, in which the weight ratio of emulsified particles of silicone to microemulsified particles of silicone ranges from 4:1 to 1:4.

5. A composition according to claim 1, in which the total amount of silicone is from 0.3 to 5%, by weight based on the total weight of the shampoo composition.

6. A composition according to claim 1, in which the cleansing surfactant is selected from anionic, amphoteric and zwitterionic surfactants, and mixtures thereof.

7. A composition according to claim 1, in which the total amount of surfactant is from 10% to 25% by weight based on the total weight of the shampoo composition.

8. A composition according to claim 1, further comprising a solid active agent selected from solid antimicrobials, preferably the heavy metal salts of pyridinethione.

9. A composition according to claim 8, in which the level of antimicrobial agent is from 0.05 to 0.8%, by weight based on the total weight of the shampoo composition.

10. A composition according to claim 1, in which the cationic deposition polymer is selected from cationic cellulose and cationic guar derivatives.

11. A composition according to claim 1, wherein the weight ratio of emulsified particles of silicone to microemulsified particles of silicone ranges from 3:1 to 1:3.

12. A composition according to claim 1, wherein the weight ratio of emulsified particles of silicone to microemulsified particles of silicone ranges from 2:1 to 1:1.

13. A composition according to claim 1, wherein the total amount of silicone is from 0.5 to 3% by weight based on the total weight of the shampoo composition.

14. A composition according to claim 8, wherein the solid active agent is zinc pyridinethione.

15. A composition according to claim 9, wherein the level of antimicrobial agent is from 0.1 to 0.5% by weight based on the total weight of the shampoo composition.

16. A composition according to claim 9, wherein the level of antimicrobial agent is about 0.3% by weight based on the total weight of the shampoo composition.

17. An aqueous shampoo composition consisting of, in addition to water:
   i) at least one cleansing surfactant;
   ii) a cationic deposition polymer; and
   iii) a silicone component consisting of a blend of:
      (a) emulsified particles of an insoluble silicone, in which the emulsified particles of insoluble silicone are incorporated into the shampoo composition as a preformed aqueous emulsion having an average silicone particle size in the emulsion and in the shampoo composition of from 0.15 to 30 microns, and
      (b) microemulsified particles of an insoluble silicone, in which the microemulsified particles of insoluble silicone are incorporated into the shampoo composition as a preformed aqueous microemulsion having an average silicone particle size in the microemulsion and in the shampoo composition of less than 0.10 microns.

* * * * *